United States Patent
Chen et al.

(10) Patent No.: US 11,381,933 B2
(45) Date of Patent: Jul. 5, 2022

(54) ENHANCED WEARABLE DEVICE OPERATION

(71) Applicant: Ford Global Technologies, LLC, Dearborn, MI (US)

(72) Inventors: Yifan Chen, Ann Arbor, MI (US); Qianyi Wang, Allen Park, MI (US)

(73) Assignee: Ford Global Technologies, LLC, Dearborn, MI (US)

( * ) Notice: Subject to any disclaimer, the term of this patent is extended or adjusted under 35 U.S.C. 154(b) by 0 days.

(21) Appl. No.: 16/634,755

(22) PCT Filed: Aug. 8, 2017

(86) PCT No.: PCT/US2017/045835
§ 371 (c)(1),
(2) Date: Jan. 28, 2020

(87) PCT Pub. No.: WO2019/032094
PCT Pub. Date: Feb. 14, 2019

(65) Prior Publication Data
US 2020/0162845 A1 May 21, 2020

(51) Int. Cl.
*H04W 4/02* (2018.01)
*H04W 4/029* (2018.01)
(Continued)

(52) U.S. Cl.
CPC ............ *H04W 4/026* (2013.01); *A61B 5/681* (2013.01); *G01C 17/20* (2013.01); *G06F 1/163* (2013.01); *G06F 1/1643* (2013.01); *H04W 4/029* (2018.02)

(58) Field of Classification Search
CPC ...... H04W 4/026; H04W 4/029; A61B 5/681; A61B 2562/0219; A61B 5/0002; A61B 5/1121; A61B 5/6802; A61B 5/7475; G01C 17/20; G06F 1/163; G06F 1/1643; G06F 2203/0381; G06F 1/1694; G06F 3/011;
(Continued)

(56) References Cited

U.S. PATENT DOCUMENTS 9,244,567 B2 1/2016 Motoi et al.
9,939,784 B1 4/2018 Berardinelli
(Continued)

FOREIGN PATENT DOCUMENTS

CN 103744280 A 4/2014
CN 103309226 B 5/2016
(Continued)

OTHER PUBLICATIONS

Dave Taylor, https://www.askdavetaylor.com/hidden-features-ios-7-compass-app/, 2014 (Year: 2014).*
(Continued)

*Primary Examiner* — Quoc Thai N Vu
(74) *Attorney, Agent, or Firm* — Brandon Hicks; Bejin Bieneman PLC

(57) ABSTRACT

A first horizontal axis of a plane of a display is determined based on a user input. Angular movement data of the display is collected. A second horizontal axis of the plane of the display is determined based on the angular movement data. A second user input on the display is mapped based on the second horizontal axis.

18 Claims, 4 Drawing Sheets

(51) Int. Cl.
*A61B 5/00* (2006.01)
*G01C 17/20* (2006.01)
*G06F 1/16* (2006.01)

(58) Field of Classification Search
CPC ...... G06F 3/04883; G06F 3/017; G06F 3/147; G06V 2201/02; G06V 40/28; G09G 3/001
See application file for complete search history.

(56) References Cited

U.S. PATENT DOCUMENTS

| | | | |
|---|---|---|---|
| 10,175,654 B2 | 1/2019 | Berardinelli | |
| 10,386,888 B2 | 8/2019 | Berardinelli | |
| 2010/0136957 A1 | 6/2010 | Horodezky et al. | |
| 2013/0100158 A1 | 4/2013 | HONJI et al. | |
| 2014/0365111 A1* | 12/2014 | McClernon | G01C 21/20 |
| | | | 701/409 |
| 2015/0128075 A1* | 5/2015 | Kempinski | G06F 3/013 |
| | | | 715/765 |
| 2016/0054791 A1 | 2/2016 | Mullins et al. | |
| 2016/0058375 A1 | 3/2016 | Rothkopf | |
| 2016/0070439 A1 | 3/2016 | Bostick et al. | |
| 2017/0024008 A1 | 1/2017 | Kienzle et al. | |
| 2018/0224804 A1 | 8/2018 | Berardinelli | |
| 2019/0146550 A1 | 5/2019 | Berardinelli | |
| 2019/0332143 A1 | 10/2019 | Berardinelli | |
| 2019/0335034 A1* | 10/2019 | Dai | G06F 3/016 |

FOREIGN PATENT DOCUMENTS

| | | |
|---|---|---|
| CN | 105868738 A | 8/2016 |
| WO | 2017/062621 A1 | 4/2017 |

OTHER PUBLICATIONS

Hodgkins, "How to use the iOS Compass for basic land navigation", https://www.engadget.com/2014-03-12-how-to-use-the-ios-compass-for-basic-land-navigation.html (Year: 2014).*
International Search Report of the International Searching Authority for PCT/US2017/045835 dated Oct. 23, 2017.

* cited by examiner

ENHANCED WEARABLE DEVICE OPERATION

BACKGROUND

Wearable devices can receive input from users. Based on the input, the wearable device can generate an instruction for a processor to perform a task. The input can be a manual input on a display of the wearable device. When the wearable device is worn on the user, the wearable device can move to one of a plurality of orientations. Differing orientations based on movement of the wearable device can cause problems in providing and receiving user input.

DETAILED DESCRIPTION

Figure 1:
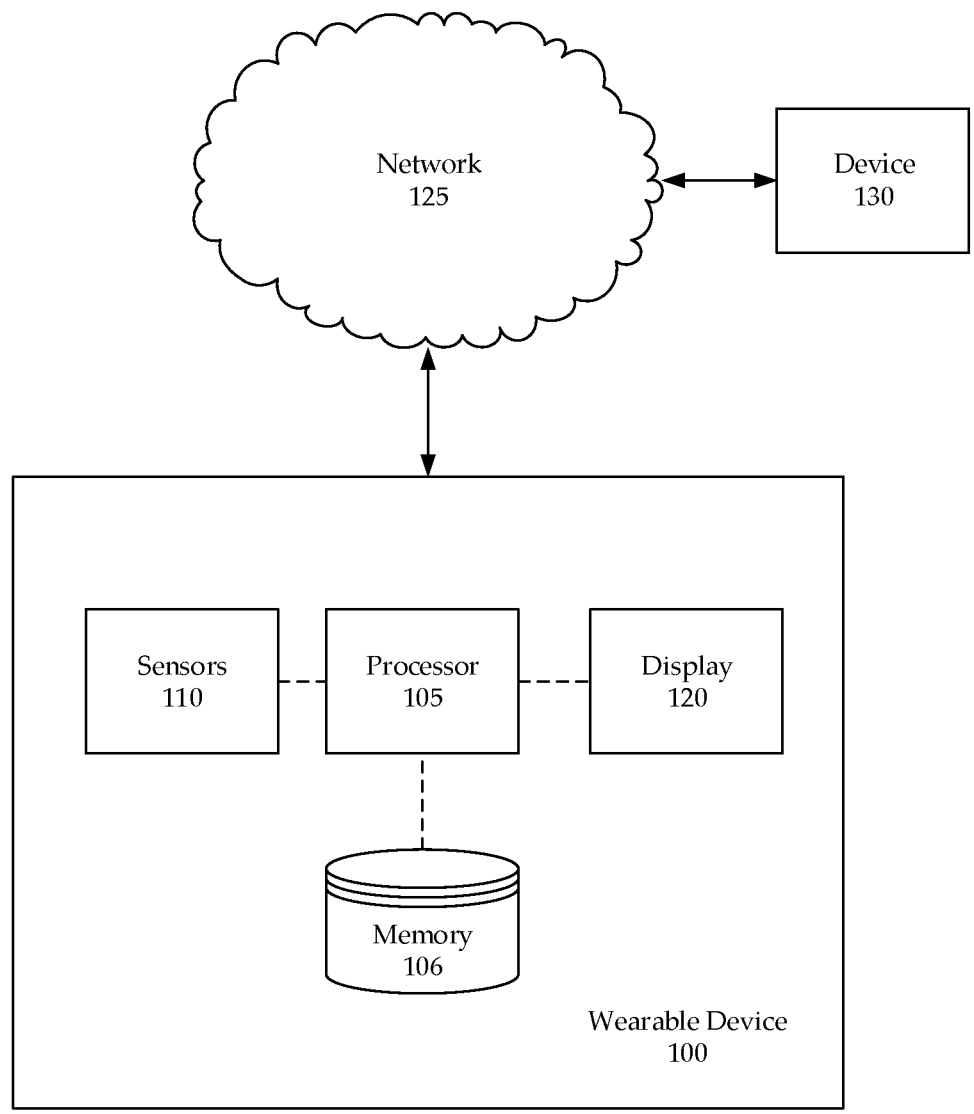
FIG. 1 is a block diagram of an example wearable device.

A system includes a computer programmed to determine a first horizontal axis of a plane of a display based on a user input, collect angular movement data of the display, determine a second horizontal axis of the plane of the display based on the angular movement data, and map a second user input on the display based on the second horizontal axis.

The computer can be further programmed to determine a rotation angle based on the angular movement data and to determine the second horizontal axis based on the rotation angle. The computer can be further programmed to determine the rotation angle based on an angular speed about an axis normal to the plane of the display.

The computer can be further programmed to project a straight line on the display based on the user input and to determine the first horizontal axis based on an angle defined between the straight line and a predetermined horizontal axis.

The computer can be further programmed to, upon detecting angular movement of the display, determine the second horizontal axis of the plane of the display. The computer can be further programmed to, upon detecting additional angular movement of the display after determining the second horizontal axis, determine a third horizontal axis based on the additional angular movement.

The computer can be further programmed to determine a vertical axis perpendicular to the second horizontal axis. The computer can be further programmed to determine the vertical axis based on the second horizontal axis and an axis normal to the plane of the display. The computer can be further programmed to, upon receiving the second user input, map the second user input based on the second horizontal axis and the vertical axis.

The computer can be further programmed to actuate a component in a second device based on the second user input.

A method includes determining a first horizontal axis of a plane of a display based on a user input, collecting angular movement data of the display, determining a second horizontal axis of the plane of the display based on the angular movement data, and mapping a second user input on the display based on the second horizontal axis.

The method can further include determining a rotation angle based on the angular movement data and determining the second horizontal axis based on the rotation angle. The method can further include determining the rotation angle based on an angular speed about an axis normal to the plane of the display.

The method can further include projecting a straight line on the display based on the user input and determining the first horizontal axis based on an angle defined between the straight line and a predetermined horizontal axis.

The method can further include, upon detecting angular movement of the display, determining the second horizontal axis of the plane of the display. The method can further include, upon detecting additional angular movement of the display after determining the second horizontal axis, determining a third horizontal axis based on the additional angular movement.

The method can further include determining a vertical axis perpendicular to the second horizontal axis. The method can further include determining the vertical axis based on the second horizontal axis and an axis normal to the plane of the display. The method can further include, upon receiving the second user input, mapping the second user input based on the second horizontal axis and the vertical axis.

The method can further include actuating a component in a second device based on the second user input.

Further disclosed is a computing device programmed to execute any of the above method steps. Yet further disclosed is a portable device comprising the computing device. Yet further disclosed is a computer program product, comprising a computer readable medium storing instructions executable by a computer processor, to execute any of the above method steps.

The display of the wearable device can have predetermined axes. In addition, based on a user input, the processor of the wearable device can determine user-defined axes. Upon receiving another input from the user, the processor can map the input from the predetermined axes to the user-defined axes. Furthermore, as the wearable device rotates with respect to one or more of the axes, the processor can determine new axes based on a rotation speed and map additional user input to the new axes. Thus, the user can provide input to the display of the wearable device without having to maintain a same orientation of the wearable device while providing the input. Furthermore, the wearable device can, based on the user input, actuate a device, e.g., a virtual reality display, a portable device, etc.

FIG. 1 illustrates an example wearable device 100. As used herein, a "wearable device" is a portable computing device including a structure so as to be wearable on a person's body (e.g., as a watch or bracelet, as a pendant, etc.), and that includes a memory, a processor, a display, and one or more input mechanisms, such as a touchscreen, buttons, etc., as well as hardware and software for wireless communications such as described herein. A wearable device 100 is of a size and shape to be fitted to or worn on a person's body, e.g., a watch-like structure including bracelet straps, etc., and as such typically has a smaller display than a user device (e.g., a smartphone, a tablet, etc.), e.g., ⅓ or ¼ of the area. For example, the wearable device 100 may be a watch, a smart watch, a vibrating apparatus, etc. that includes capabilities for wireless communications using IEEE 802.11, Bluetooth®, BLE, and/or cellular communications protocols. Further, the wearable device 100 may use such communications capabilities to communicate via a network, e.g., using Bluetooth®.

The wearable device 100 includes a wearable device processor 105 and a memory 106. The processor 105 is implemented via circuits, chips, or other electronic component that can receive the data from the sensors 110 and determine, from the data, the orientation of the wearable device 100. The processor 105 can be programmed to process the sensor 110 data. Processing the data may include processing the acceleration or other data captured by the sensors 110 to determine the angular movement of the wearable device 100.

The memory 106 may be of any known type, e.g., hard disk drives, solid state drives, servers, or any volatile or non-volatile media. The memory 106 may store the collected data sent from the sensors 110.

The wearable device 100 includes one or more sensors 110. Sensors 110 may include a variety of devices. For example, as is known, various controllers in the wearable device 100 may operate as sensors 110 to provide data via a wearable device 100 network or bus, e.g., data relating to wearable device 100 position, speed, rotation, acceleration, etc. Further, other sensors 110 could include cameras, motion detectors, biometric detectors, etc., i.e., sensors 110 to provide data for evaluating a location of an object, determining the presence of a user, etc. The sensors 110 can communicate with the processor 105.

The wearable device 100 includes a display 120. The display 120 can receive user input, e.g., as a touchscreen display. The display 120 can define a plane that the processor 105 can use to map the user input to an instruction to actuate one or more wearable device 100 components. The user input can be a swiping motion across the display 120.

The wearable device 100 may be in communication with a network 125. The processor 105 may further be programmed to communicate with one or more remote sites such as a device 130, e.g., a virtual reality display, a portable device, etc. The network 125 represents one or more mechanisms by which a vehicle computer may communicate with the device 130. Accordingly, the network 125 may be one or more of various wired or wireless communication mechanisms, including any desired combination of wired (e.g., cable and fiber) and/or wireless (e.g., cellular, wireless, satellite, microwave, and radio frequency) communication mechanisms and any desired network topology (or topologies when multiple communication mechanisms are utilized). Exemplary communication networks include wireless communication networks (e.g., using Bluetooth®, Bluetooth® Low Energy (BLE), IEEE 802.11, local area networks (LAN) and/or wide area networks (WAN), including the Internet, providing data communication services.

The wearable device 100 may be in communication with a second device 130. The device 130 can include a processor and a memory. The device 130 can be, e.g., a virtual reality display, a portable device, etc. The wearable device 100 can instruct the processor of the device 130 to actuate one or more components, e.g., a display, an alert, etc.

Figure 2:
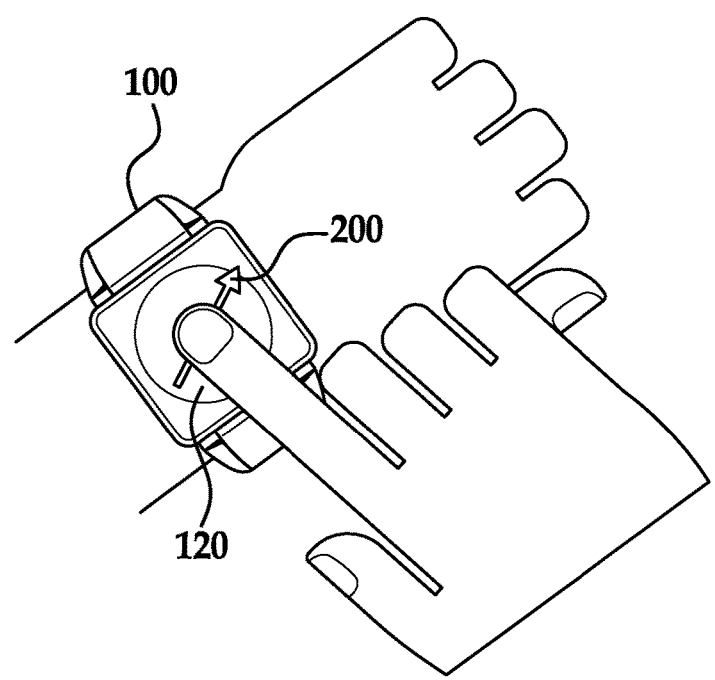
FIG. 2 illustrates receiving user input to the example wearable device to determine a first set of axes.

FIG. 2 illustrates the wearable device 100 receiving user input 200. The user input 200 can be a tactile input extending across the display 120 measured by one or more sensors 110 in the wearable device 100. The processor 105 can prompt the user for input 200. By providing an initial input, the processor 105 can determine axes for the display 120 to map future user input. The processor 105 can prompt the user using, e.g., a visual indicator on the display 120, an audio cue, a haptic cue, etc. The processor 105 can receive input on the display 120, e.g., as a swiping motion across the display 120 such as shown by the arrow representing the input 200.

Figure 3:
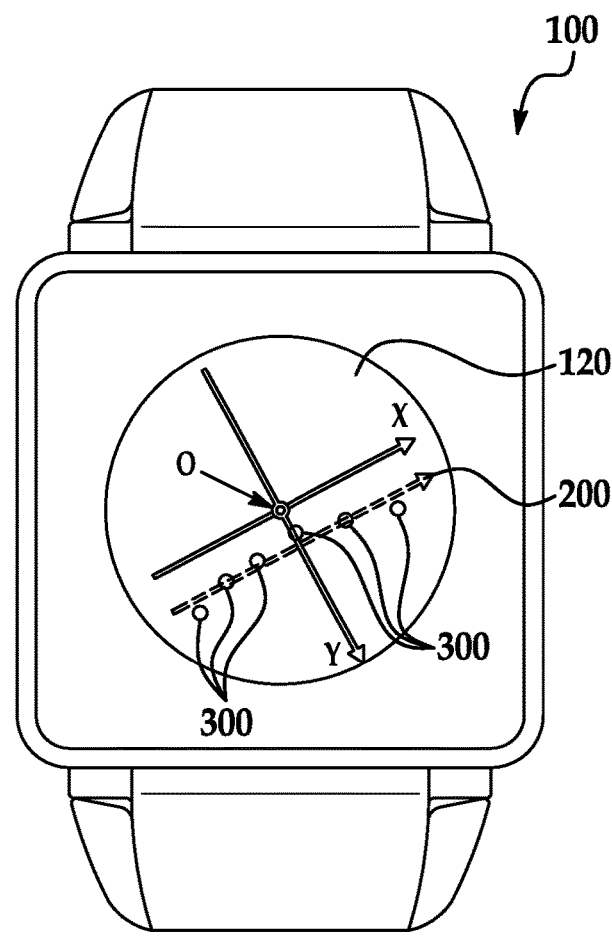
FIG. 3 illustrates mapping the first set of axes based on the user input.
Figure 4:
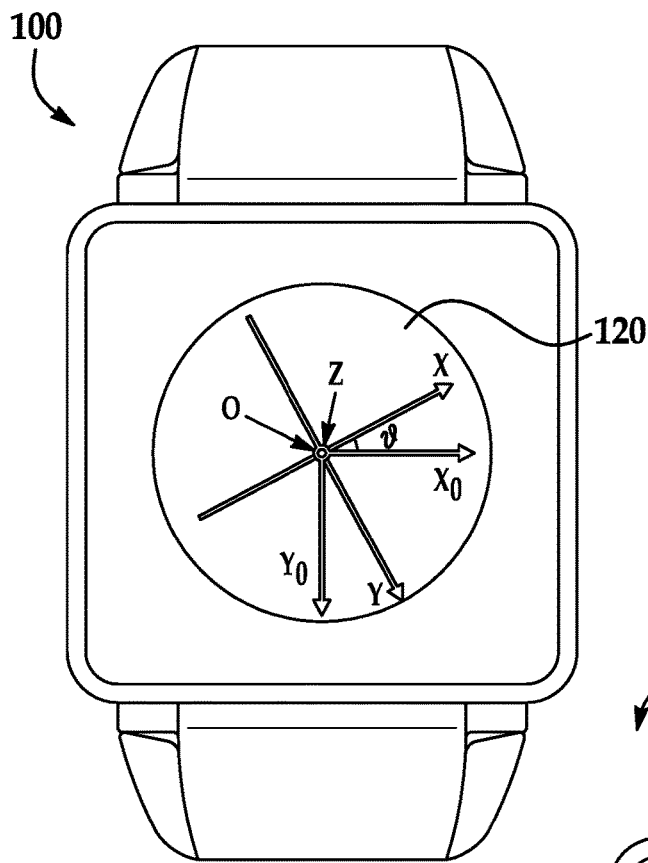
FIG. 4 illustrates determining a rotation angle based on the first set of axes.

FIG. 3 illustrates the processor 105 mapping the input 200 on the display 120 to a horizontal axis X. The display 120 includes a center point O. The center point O is a fixed point on the display 120 defining horizontal and vertical axes, as described below. The display 120 can have predetermined display axes $X_0$, $Y_0$, Z extending through the center point O, as shown in FIG. 4. The display axis $X_0$ is a horizontal axis. The display axis $Y_0$ extends perpendicular to the display horizontal axis $X_0$, and is a vertical axis. The axis Z extends normal to the display 120 through the center point O, e.g., using the right-hand rule with the axes $X_0$, $Y_0$. The display axes $X_0$, $Y_0$ are defined in a plane of the display 120, and the axis Z extends normal to the plane of the display 120.

The processor 105 can project a straight line extending through the received user input 200. The user input 200 can be received as a series of discrete points 300 on the display 120 indicating portions of the display 120 contacted by the user. The wearable device processor 105 can determine the line extending through the discrete points 300 using known regression techniques, e.g., a least-squares fit. If the line does not extend through the center point O, the processor 105 can map the line defined by the user input 200 to the horizontal axis X through the center point O. The processor 105 can determine a line that is parallel to the input 200 and extends through the center point O and define the line as the horizontal axis X.

The processor 105 can define a horizontal axis X based on the line extending through the user input. The horizontal axis X can be the axis extending through the center O parallel to the line. The wearable device processor 105 can define a vertical axis Y that is perpendicular to the horizontal axis X and extends through the center O.

FIG. 4 illustrates a rotation angle θ defined by the horizontal axis X. The display 120 can have the display horizontal axis $X_0$ and the display vertical axis $Y_0$. The horizontal axis X can define the rotation angle θ with the display horizontal axis $X_0$. The processor 105 can compare the horizontal axis X to the display horizontal axis $X_0$ to determine the rotation angle θ. For example, the processor 105 can compare pixels on the display 120 corresponding to the horizontal axis X and, using known trigonometric techniques, determine the angle θ between the pixels defining the horizontal axis X and the display horizontal axis $X_0$.

The processor 105 can map input on the display based on the rotation angle θ. When the user provides input to the display 120, the processor 105 can map (e.g., as shown in Equation 1 below) the input from the rotated axes X, Y to the display axes $X_0$, $Y_0$:

$$\begin{bmatrix} X \\ Y \end{bmatrix} = \begin{bmatrix} \cos(\theta) & -\sin(\theta) \\ \sin(\theta) & \cos(\theta) \end{bmatrix} \begin{bmatrix} X_0 \\ Y_0 \end{bmatrix} \quad (1)$$

Upon receiving input on the display 120, the processor 105 can record the input as a set of coordinates defined along the rotated axes X, Y. The processor 105 can map the input to the display axes $X_0$, $Y_0$ with the rotation angle θ according to Equation 1 above. Thus, input to the display 120 can be processed according to the user-defined axes X, Y. The processor 105 can instruct another device (not shown), e.g., a virtual reality display, a portable device, etc., based on the input mapped to the user-defined axes X, Y.

Figure 5:
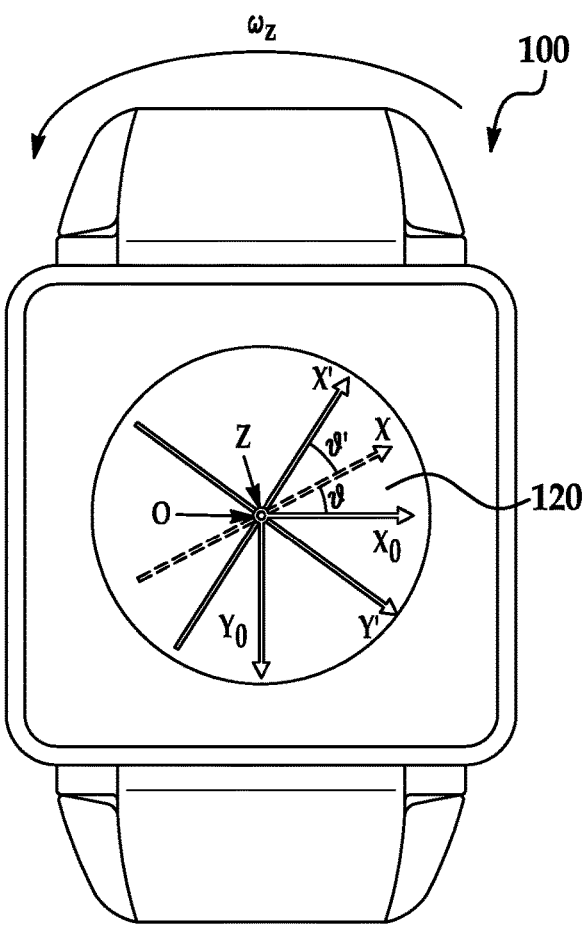
FIG. 5 illustrates defining a second set of axes based on the user input and rotation of the wearable device.

FIG. 5 illustrates the wearable device 100 rotating about the axis Z. The processor 105 can collect data about angular movement of the display about the axis Z. Angular speed data $\omega_Z$, measured in radians/second, can be collected with a sensor 110 (e.g., a gyroscope, an accelerometer, etc.) for a predetermined period of time T, e.g., 500 ms. The processor 105 can, using known techniques, determine a rotation angle $\theta'$ relative to the horizontal axis X based on the angular speed data $\omega_Z$. For example, the wearable device processor 105 can use numerical integration techniques over the period of time T to determine the rotation angle $\theta'$, i.e.:

$$\theta' = \int_0^T \omega_Z dt \qquad (2)$$

The processor 105 can determine a second horizontal axis X' and a second vertical axis Y' based on the rotation angle $\theta'$. The axis Z is normal to the display 120 and to the axes X', Y'. That is, input received on the display 120 according to the axes X', Y' can be mapped to the device axes $X_0$, $Y_0$ according to the following formula:

$$\begin{bmatrix} X' \\ Y' \end{bmatrix} = \begin{bmatrix} \cos(\theta' + \theta) & -\sin(\theta' + \theta) \\ \sin(\theta' + \theta) & \cos(\theta' + \theta) \end{bmatrix} \begin{bmatrix} X_0 \\ Y_0 \end{bmatrix} \qquad (3)$$

Upon detecting a nonzero value for $\omega_Z$, the processor 105 can determine to determine the second axes X', Y'. That is, when the processor 105 detects angular movement of the wearable device 100, the processor 105 can determine new axes X', Y' and map user input from the axes X', Y'. That is, the axes X', Y' can be updated whenever $\theta'$ is detected to change. The processor 105 can be programmed to update the axes X', Y' when the detected change in the rotation angle $\theta'$ is greater than a predetermined threshold, e.g., 1 degree.

The processor 105 can be programmed to receive a second user input (not shown inasmuch as the second user input could be shown in a manner as the input 200 is shown) to define the second horizontal axis X'. As described above, the user can provide a tactile input across the display 120, and the processor 105 can map the user input to the second horizontal axis X' and the second vertical axis Y'. The processor 105 can determine to prompt the user for the second user input when, e.g., the user requests to reset the axes X', Y', the wearable device 100 has been powered down and restarted, etc.

Figure 6:
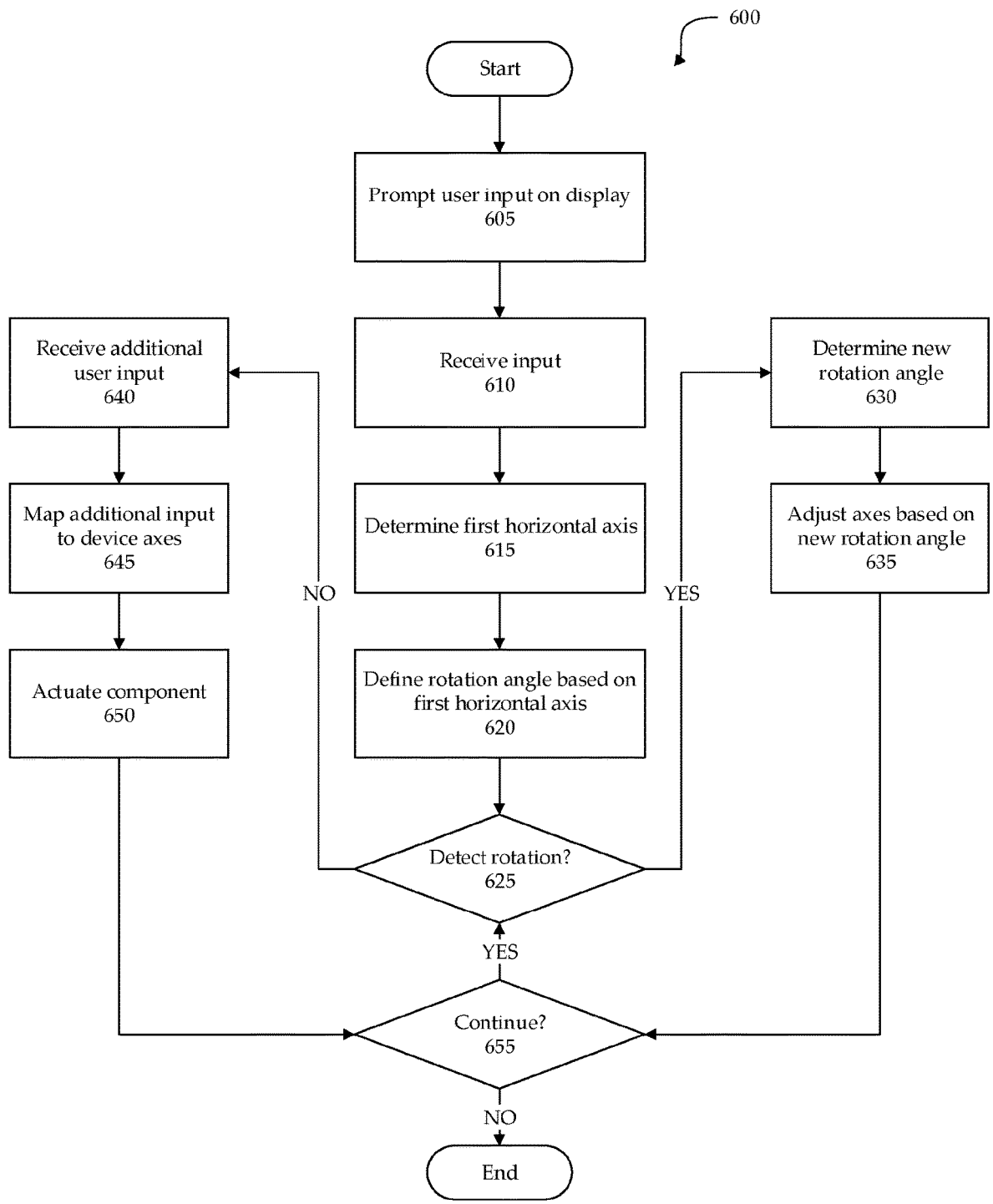
FIG. 6 illustrates an example process for determining axes of the wearable device.

FIG. 6 illustrates an example process 600 for operating a wearable device 100. The process 600 begins in a block 605, in which the processor 105 prompts the user to provide an input 200 to the display 120 to define a first horizontal axis X. The processor 105 can provide a prompt, e.g., a visual cue, an aural tone, etc., to instruct the user to provide input 200 to the display 120.

Next, in a block 610, the processor 105 receives the input 200 to the display 120. As described above, the user can provide an input 200 approximating a straight line on the display 120. The display 120 can include one or more sensors 110, e.g., capacitive sensors 110, that can detect portions of the display 120 contacted by the user.

Next, in a block 615, the processor 105 can determine a first horizontal axis X based on the input 200. The processor 105 can determine a line through discrete points 300 of the input 200 using known techniques, e.g., a least-squares calculation. The processor 105 can define the axis X that is parallel to the line and extends through the origin O. The processor 105 can further determine the first vertical axis Y as the axis perpendicular to the horizontal axis X.

Next, in a block 620, the processor 105 can determine a rotation angle $\theta$ based on the first horizontal axis X. The processor 105 can compare the first horizontal axis X to a predetermined device horizontal axis $X_0$ and define the rotation angle $\theta$ between the horizontal axes X, $X_0$. The processor 105 can then map inputs to the display 120 based on the rotation angle $\theta$, as described above, to the axes X, Y.

Next, in a block 625, the processor 105 determines whether one of the sensors 110 detects rotation data $\omega_Z$. As described above, as the wearable device 100 rotates about the axis Z, the sensors 110 (e.g., an accelerometer, a gyroscope, etc.) can detect the rotation of the wearable device 100 about the axis Z. If the processor 105 detects rotation, the process 600 continues in a block 630. Otherwise, the process 600 continues in a block 640.

In the block 630, the processor 105 collects rotation data $\omega_Z$ and determines a new rotation angle $\theta'$ based on the rotation data $\omega_Z$. As described above, the processor 105 can use integration techniques (e.g., numerical integration) to determine a change in the orientation of the wearable device 100 based on a measured angular speed $\omega_Z$ determined from an accelerometer 110.

Next, in a block 635, the processor 105 determines a second horizontal axis X' and a second vertical axis Y' based on the rotation angle $\theta'$. As described above, the second horizontal axis X' is the axis rotated about the rotation angle $\theta'$ from the horizontal axis X. The process 600 continues in a block 655.

In the block 640, the processor 105 receives an additional user input on the display 120. The user can provide input to the display 120 of the wearable device 100 to, e.g., actuate a component in a second device (a virtual reality device, a portable device, etc.). The additional user input can be subsequent to the user input defining the axes X, Y, and the processor 105 can be programmed to actuate the component in the second device according to the additional user input.

Next, in a block 645, the processor 105 maps the additional user input to the device axes $X_0$, $Y_0$. As described above, based on the rotation angle $\theta$, $\theta'$, the processor 105 can map the additional user input (e.g., using Equations 1, 3 shown above) to the device axes $X_0$, $Y_0$. Thus, the user can provide input to the display 120 of the wearable device 100 without having to maintain a same orientation as that of the wearable device 100 while providing the input.

Next, in a block 650, the processor 105 actuates a component in a second device 130. The processor 105 can communicate with the second device 130 over the network 125 to actuate the component in the second device 130. For example, the processor 105 can actuate a virtual reality display to display one or more items. In another example, the processor 105 can actuate a processor in a portable device to operate programming.

In the block 655, the processor 105 determines whether to continue the process 600. For example, the processor 105 can determine to continue the process 600 when the wearable device 100 is still in communication with the second device 130. If the processor 105 determines to continue, the process 600 returns to the block 625 to determine if the wearable device 100 has rotated. Otherwise, the process 600 ends.

As used herein, the adverb "substantially" modifying an adjective means that a shape, structure, measurement, value, calculation, etc. may deviate from an exact described geometry, distance, measurement, value, calculation, etc., because of imperfections in materials, machining, manufacturing, data collector measurements, computations, processing time, communications time, etc.

Computers, including the processor 105 and the memory 106, generally each include instructions executable by one or more computers such as those identified above, and for carrying out blocks or steps of processes described above. Computer-executable instructions may be compiled or interpreted from computer programs created using a variety of programming languages and/or technologies, including, without limitation, and either alone or in combination, Java™, C, C++, Visual Basic, Java Script, Perl, HTML, etc. In general, a processor (e.g., a microprocessor) receives instructions, e.g., from a memory, a computer-readable medium, etc., and executes these instructions, thereby performing one or more processes, including one or more of the processes described herein. Such instructions and other data may be stored and transmitted using a variety of computer-readable media. A file in the computer is generally a collection of data stored on a computer readable medium, such as a storage medium, a random access memory, etc.

A computer-readable medium includes any medium that participates in providing data (e.g., instructions), which may be read by a computer. Such a medium may take many forms, including, but not limited to, non-volatile media, volatile media, etc. Non-volatile media include, for example, optical or magnetic disks and other persistent memory. Volatile media include dynamic random access memory (DRAM), which typically constitutes a main memory. Common forms of computer-readable media include, for example, a floppy disk, a flexible disk, hard disk, magnetic tape, any other magnetic medium, a CD-ROM, DVD, any other optical medium, punch cards, paper tape, any other physical medium with patterns of holes, a RAM, a PROM, an EPROM, a FLASH-EEPROM, any other memory chip or cartridge, or any other medium from which a computer can read.

With regard to the media, processes, systems, methods, etc. described herein, it should be understood that, although the steps of such processes, etc. have been described as occurring according to a certain ordered sequence, such processes could be practiced with the described steps performed in an order other than the order described herein. It further should be understood that certain steps could be performed simultaneously, that other steps could be added, or that certain steps described herein could be omitted. For example, in the process 600, one or more of the steps could be omitted, or the steps could be executed in a different order than shown in FIG. 6. In other words, the descriptions of systems and/or processes herein are provided for the purpose of illustrating certain embodiments, and should in no way be construed so as to limit the disclosed subject matter.

Accordingly, it is to be understood that the present disclosure, including the above description and the accompanying figures and below claims, is intended to be illustrative and not restrictive. Many embodiments and applications other than the examples provided would be apparent to those of skill in the art upon reading the above description. The scope of the invention should be determined, not with reference to the above description, but should instead be determined with reference to claims appended hereto and/or included in a non-provisional patent application based hereon, along with the full scope of equivalents to which such claims are entitled. It is anticipated and intended that future developments will occur in the arts discussed herein, and that the disclosed systems and methods will be incorporated into such future embodiments. In sum, it should be understood that the disclosed subject matter is capable of modification and variation.

The article "a" modifying a noun should be understood as meaning one or more unless stated otherwise, or context requires otherwise. The phrase "based on" encompasses being partly or entirely based on.

What is claimed is:

1. A system, comprising a computer programmed to:
   determine a first horizontal axis of a plane of a display based on a user input, the first horizontal axis being rotated relative to a default horizontal axis of the display by a first rotation angle, the first horizontal axis mapping input to the display to the default horizontal axis of the display;
   collect angular movement data of the display;
   determine a second horizontal axis of the plane of the display that is rotated relative to the first horizontal axis by a second rotation angle that is based on the angular movement data; and
   map a second user input on the display from the second horizontal axis to the default horizontal axis of the display.

2. The system of claim 1, wherein the computer is further programmed to determine the second rotation angle based on an angular speed about an axis normal to the plane of the display.

3. The system of claim 1, wherein the computer is further programmed to project a straight line on the display based on the user input and to determine the first horizontal axis based on an angle defined between the straight line and a predetermined horizontal axis.

4. The system of claim 1, wherein the computer is further programmed to, upon detecting angular movement of the display, determine the second horizontal axis of the plane of the display.

5. The system of claim 4, wherein the computer is further programmed to, upon detecting additional angular movement of the display after determining the second horizontal axis, determine a third horizontal axis based on the additional angular movement.

6. The system of claim 1, wherein the computer is further programmed to determine a vertical axis perpendicular to the second horizontal axis.

7. The system of claim 6, wherein the computer is further programmed to determine the vertical axis based on the second horizontal axis and an axis normal to the plane of the display.

8. The system of claim 7, wherein the computer is further programmed to, upon receiving the second user input, map the second user input based on the second horizontal axis and the vertical axis.

9. The system of claim 1, wherein the computer is further programmed to actuate a component in a second device based on the second user input.

10. A method, comprising:
    determining a first horizontal axis of a plane of a display based on a user input, the first horizontal axis being rotated relative to a default horizontal axis of the display by a first rotation angle, the first horizontal axis mapping input to the display to the default horizontal axis of the display;
    collecting angular movement data of the display;
    determining a second horizontal axis of the plane of the display that is rotated relative to the first horizontal axis by a second rotation angle that is based on the angular movement data; and mapping a second user input on the display from the second horizontal axis to the default horizontal axis of the display.

11. The method of claim 10, further comprising determining the second rotation angle based on an angular speed about an axis normal to the plane of the display.

12. The method of claim 10, further comprising projecting a straight line on the display based on the user input and determining the first horizontal axis based on an angle defined between the straight line and a predetermined horizontal axis.

13. The method of claim 10, further comprising, upon detecting angular movement of the display, determining the second horizontal axis of the plane of the display.

14. The method of claim 13, further comprising, upon detecting additional angular movement of the display after determining the second horizontal axis, determining a third horizontal axis based on the additional angular movement.

15. The method of claim 10, further comprising determining a vertical axis perpendicular to the second horizontal axis.

16. The method of claim 15, further comprising determining the vertical axis based on the second horizontal axis and an axis normal to the plane of the display.

17. The method of claim 16, further comprising, upon receiving the second user input, mapping the second user input based on the second horizontal axis and the vertical axis.

18. The method of claim 10, further comprising actuating a component in a second device based on the second user input.

* * * * *